US012602786B2

(12) United States Patent
Ghoshal et al.

(10) Patent No.: US 12,602,786 B2
(45) Date of Patent: Apr. 14, 2026

(54) FREE FLUID ESTIMATION

(71) Applicant: KONINKLIJKE PHILIPS N.V.,
Eindhoven (NL)

(72) Inventors: Goutam Ghoshal, South Grafton, MA
(US); Balasundar Iyyavu Raju, North
Andover, MA (US); Jonathan Fincke,
Belmont, MA (US)

(73) Assignee: KONINKLIJKE PHILIPS N.V.,
Eindhoven (NL)

( * ) Notice: Subject to any disclaimer, the term of this
patent is extended or adjusted under 35
U.S.C. 154(b) by 440 days.

(21) Appl. No.: 18/129,307

(22) Filed: Mar. 31, 2023

(65) Prior Publication Data

US 2023/0316523 A1 Oct. 5, 2023

Related U.S. Application Data

(60) Provisional application No. 63/326,654, filed on Apr.
1, 2022.

(51) Int. Cl.
| | |
|---|---|
| *G06K 9/00* | (2022.01) |
| *G06T 7/00* | (2017.01) |
| *G16H 10/60* | (2018.01) |
| *G16H 30/40* | (2018.01) |

(52) U.S. Cl.
CPC ........... *G06T 7/0014* (2013.01); *G16H 10/60*
(2018.01); *G16H 30/40* (2018.01); *G06T*
*2207/10132* (2013.01); *G06T 2207/20081*
(2013.01); *G06T 2207/20084* (2013.01); *G06T*
*2207/30004* (2013.01)

(58) Field of Classification Search
CPC ......... G06T 7/0014; G06T 2207/10132; G06T
2207/20081; G06T 2207/20084; G06T
2207/30004; G06T 7/62; G06T
2207/10081; G06T 2207/10088; G06T
2207/30101; G06T 7/0012; G16H 10/60;
G16H 30/40; G16H 50/20
See application file for complete search history.

(56) References Cited

U.S. PATENT DOCUMENTS

| | | | |
|---|---|---|---|
| 2015/0201907 A1* | 7/2015 | Stergiopoulos .... | A61B 5/02042 |
| | | | 600/371 |
| 2022/0293243 A1* | 9/2022 | Callcut ................. | A61B 8/085 |

* cited by examiner

*Primary Examiner* — Xin Jia

(57) ABSTRACT

The present disclosure provides techniques for free fluid
estimation including identifying a region of free fluid in an
diagnostic image, calculating a free fluid measure based on
the region of free fluid identified in the diagnostic image,
and generating a volume class for the region of free fluid in
the diagnostic image, wherein the volume class is generated
by comparison of the free fluid measure to a data set of
previously stored free fluid measures. The present disclosure
may be implemented as a method, in a device, a computer
readable medium, and a system, among other form factors.

17 Claims, 5 Drawing Sheets

FREE FLUID ESTIMATION

CROSS-REFERENCE TO RELATED APPLICATIONS

This application claims the benefit and priority of Application No. 63/326,654 filed on Apr. 1, 2022, the entire contents of which are incorporated herein by reference.

GOVERNMENT INTEREST

This invention was made with United States government support awarded by the United States Department of Health and Human Services under the grant number HHS/ASPR/BARDA 75A50120000097. The United States has certain rights in this invention.

BACKGROUND

Focused Assessment with Sonography in Trauma (FAST) exams are used as a rapid bedside imaging tool to screen for internal bleeding such as around the heart or in the abdomen especially after trauma. Internal bleeding refers to blood that collects inside the body and is not visible from the outside the body. Severe internal bleeding can cause hemorrhagic shock or death if proper medical treatment isn't provided quickly. The FAST exam by ultrasound focuses on identifying free intraperitoneal or pericardial fluid in trauma examination.

SUMMARY OF THE INVENTION

The present disclosure relates to free fluid estimation. In particular, the present disclosure relates, in part, to the automation of free fluid estimation through anatomical identifications to provide quantified readings, results along a relative scale, and other outputs to assist in exam interpretation.

DETAILED DESCRIPTION OF THE EMBODIMENTS

Figure 1:
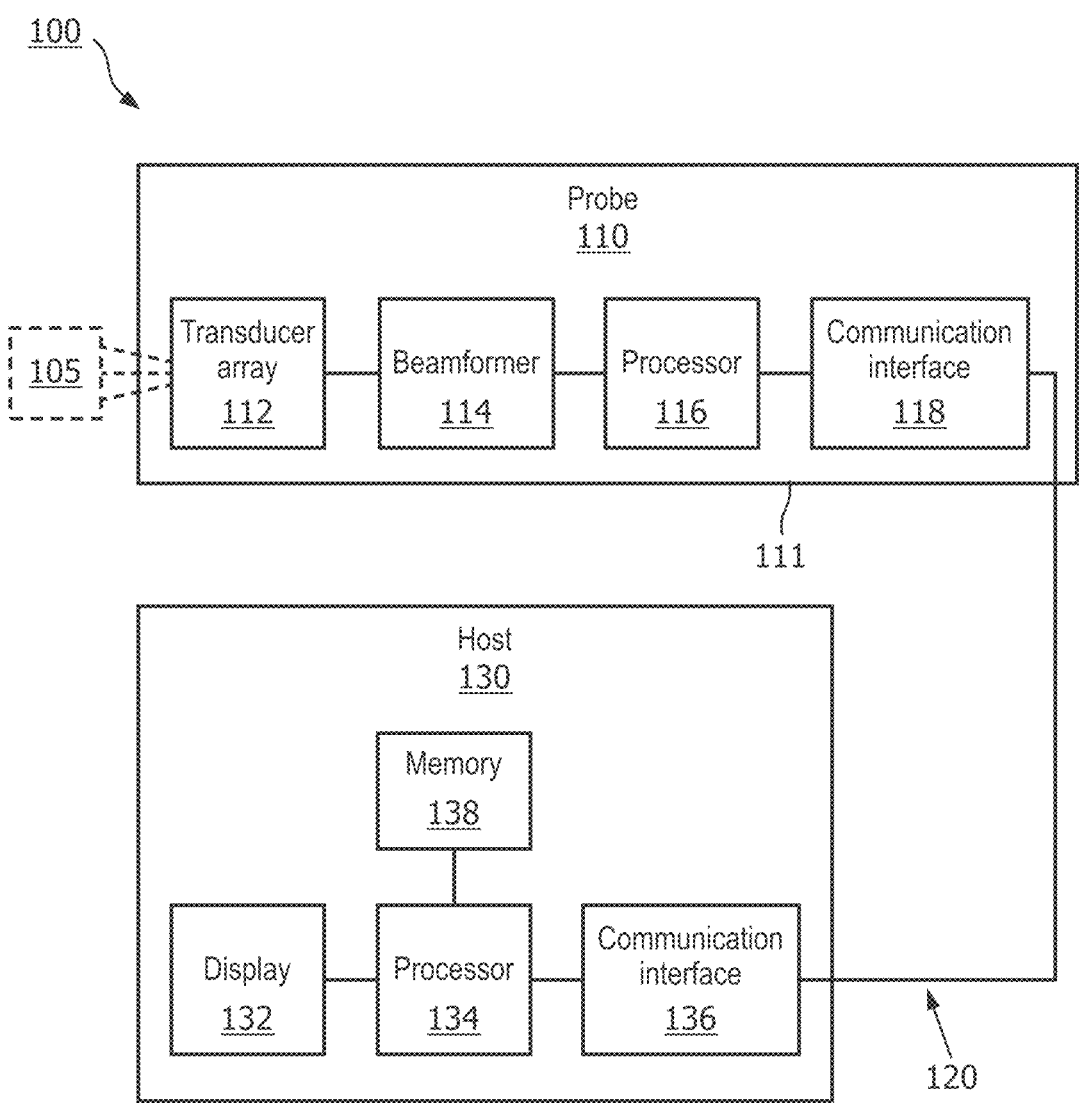
FIG. 1 illustrates a schematic, diagrammatic representation of an imaging system, according to aspects of the present disclosure.

Imaging devices and systems can be used as a standard of care for imaging internal bleeding such as around the heart or in the abdomen after trauma. The present disclosure includes examples related to the FAST exam, however the concepts discussed are general and can be applied to other applications.

Quick assessment of internal bleeding and its severity level can be a valuable screening tool, quickly understand the risk to the patient, and transport them to the appropriate facility for the respective treatment management. For example, a patient with excessive fluid and internal bleeding will benefit from more immediate intervention. Using FAST in combination with Artificial Intelligence (AI) for abdominal bleeding detection can assist early detect and estimate the level of fluids, and contribute to the prioritization of rapid evaluation, early intervention and have the potential of improving the survival rate and/or outcome of a patient.

Abdominal FAST exams can be performed on the right upper quadrant (RUQ) of a patient, a left upper quadrant (LUQ), and along the suprapubic region. Additional views in a FAST exam may also include scanning the cardiac regions and the lungs. Formal interpretation by a trained clinician can be costly or result in delays in results due to limited clinician time. Interpretation of imaging scans may be used to develop a plan of treatment.

The present disclosure provides techniques for automatically estimating a level of free fluid volume during the FAST exam and provides that information to the user in formats that include not only a quantification of the free fluid, but may also include a relative result which places the free fluid amount in context. The present disclosure further relates to the detection of at least one image frame that detects the highest area of free fluid compared to other frames captured for a particular patient and saving that particular frame. The saved image may be formatted for use in medical documentation or stored and used in identifying the correct billing codes suitable based on the detected scope and scale of the issue being detected. These techniques may be used in a variety of ultrasound formats including general ultrasound, point-of-care ultrasound, handheld devices, or other formats.

Automated detection of free fluid and an estimate of its volume can define the plan of treatment for the patient and improve patient survival rate by reducing time between a scan and actionable interpretation of the received signals. Using FAST in combination with artificial intelligence for abdominal bleeding detection may assist in the early detection of free fluids but also the estimation of the relative level of free fluids thereby contributing to rapid evacuation and early intervention for cases where it may be warranted. The present disclosure provides examples that use anatomical features that are automatically detected to predict, among other measures, an estimation of the area and/or volume of the free fluid. In an example, the present techniques disclose a method for identifying a volume class of the free fluid identified.

In some circumstances, the FAST exam can be taught as a binary exam. The present techniques enable not only binary classification but also estimation of volume, area, both in quantified readings as well as relative readings. In the present techniques, the results of these exams can be displayed on the frame. Further, a frame captured with the largest estimated free fluid area from an ultrasound video may also be saved and/or displayed. This captured frame may be saved, formatted, displayed, and/or prepared for documentation and billing purposes.

The present techniques may also enable the classification of free fluid volume into a number of volume classes. In some examples, the function of the disclosed techniques may be activated in response to a detection of free fluid flow while conducting a number of different exams including scans other than FAST exams. In another example, the display of free fluid quantification or relative readings may be provided in response to a detection of free fluid and not displayed otherwise. In an example, if a FAST exam was a selected mode on an ultrasound device, the free fluid estimation and results display would appear in response to a detection of free fluid and would not be displayed if no free fluid was detected in an ultrasound image.

The present example may include ultrasound devices that are handheld, cart-based, may have a display or may be interoperable with a variety of components that enable the acquisition of ultrasound signals to form ultrasound images. In some instances, the display of results of the present techniques may be displayed on a display device that is part of a larger system, in other cases, the results may be sent to another device for display, and in another example, the results may be stored locally or remotely. Results of a free fluid estimation may be used in identifying an appropriate level of billing for medical procedures. Results from free fluid estimation may be used and stored as part of medical records and associated with a patient, provider, time, facility, among other information relative to the capture of the images, the patient and their relevant information, the provider, and the medical system at which the exam was administered. In an example, the present techniques may be used in two dimensional (2D) or three dimensional (3D) ultrasound imaging as well as other ultrasound formats. The combination of the below methods into a single method with a decision point reduces the number of tests needed to be performed by a machine as rather than performing two full scans, the decision point as to the appropriate examination reduces redundancy in processing. The proposed solution described technically enables the display of relative scale and absolute scale for free fluid during the time in which data is still being gathered by for example an ultrasound transducer. This proposed solution to estimate area of free fluid in a frame impacts the functioning of the machine as it displays free fluid information based on image analysis rather than on user inputs roughly defining a particular region a user may believe includes free fluid. The proposed solution reduces operation time and energy consumption of a processing device and memory from faster administration of an exam and identification of free fluid regions including estimations about the character and size of the same.

FIG. 1 is a schematic, diagrammatic representation of an ultrasound imaging system 100, according to aspects of the present disclosure. The ultrasound imaging system 100 may for example be used to acquire ultrasound video clips that may be used to train the ultrasound video feature classification system, or that may be analyzed and highlighted in a clinical setting (whether in real time, near-real time, or as post-processing of stored video clips) by the ultrasound video feature classification system.

The ultrasound imaging system 100 is used for scanning an area or volume of a subject's body. A subject may include a patient of an ultrasound imaging procedure, or any other person, or any suitable living or non-living organism or structure. The ultrasound imaging system 100 includes an ultrasound imaging probe 110 in communication with a host 130 over a communication interface or link 120. The probe 110 may include a transducer array 112, a beamformer 114, a processor circuit 116, and a communication interface 118. The host 130 may include a display 132, a processor circuit 134, a communication interface 136, and a memory 138 storing subject information.

In some aspects, the probe 110 is an external ultrasound imaging device including a housing 111 configured for handheld operation by a user. The transducer array 112 can be configured to obtain ultrasound data while the user grasps the housing 111 of the probe 110 such that the transducer array 112 is positioned adjacent to or in contact with a subject's skin. The probe 110 is configured to obtain ultrasound data of anatomy within the subject's body while the probe 110 is positioned outside of the subject's body for general imaging, such as for abdomen imaging, liver imaging, etc. In some aspects, the probe 110 can be an external ultrasound probe, a transthoracic probe, and/or a curved array probe.

In other aspects, the probe 110 can be an internal ultrasound imaging device and may comprise a housing 111 configured to be positioned within a lumen of a subject's body for general imaging, such as for abdomen imaging, liver imaging, etc. In some aspects, the probe 110 may be a curved array probe. Probe 110 may be of any suitable form for any suitable ultrasound imaging application including both external and internal ultrasound imaging.

In some aspects, aspects of the present disclosure can be implemented with medical images of subjects obtained using any suitable medical imaging device and/or modality. Examples of medical images and medical imaging devices include x-ray images (angiographic images, fluoroscopic images, images with or without contrast) obtained by an x-ray imaging device, computed tomography (CT) images obtained by a CT imaging device, positron emission tomography—computed tomography (PET-CT) images obtained by a PET-CT imaging device, magnetic resonance images (MRI) obtained by an MM device, single-photon emission computed tomography (SPECT) images obtained by a SPECT imaging device, optical coherence tomography (OCT) images obtained by an OCT imaging device, and intravascular photoacoustic (IVPA) images obtained by an IVPA imaging device. The medical imaging device can obtain the medical images while positioned outside the subject body, spaced from the subject body, adjacent to the subject body, in contact with the subject body, and/or inside the subject body.

For an ultrasound imaging device, the transducer array 112 emits ultrasound signals towards an anatomical object 105 of a subject and receives echo signals reflected from the object 105 back to the transducer array 112. The ultrasound transducer array 112 can include any suitable number of acoustic elements, including one or more acoustic elements and/or a plurality of acoustic elements. In some instances, the transducer array 112 includes a single acoustic element. In some instances, the transducer array 112 may include an array of acoustic elements with any number of acoustic elements in any suitable configuration. For example, the transducer array 112 can include between 1 acoustic element and 10000 acoustic elements, including values such as 2 acoustic elements, 4 acoustic elements, 36 acoustic elements, 64 acoustic elements, 128 acoustic elements, 500 acoustic elements, 812 acoustic elements, 1000 acoustic elements, 3000 acoustic elements, 8000 acoustic elements, and/or other values both larger and smaller. In some instances, the transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) can be uniformly or independently controlled and activated. The transducer array 112 can be configured to obtain one-dimensional, two-dimensional, and/or three-dimensional images of a subject's anatomy. In some aspects, the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The object 105 may include any anatomy or anatomical feature, such as a kidney, liver, and/or any other anatomy of a subject. The present disclosure can be implemented in the context of any number of anatomical locations and tissue types, including without limitation, organs including the liver, kidneys, gall bladder, pancreas, lungs; ducts; intestines; nervous system structures including the brain, dural sac, spinal cord and peripheral nerves; the urinary tract; as well as valves within the blood vessels, blood, abdominal organs, and/or other systems of the body. In some aspects, the object 105 may include malignancies such as tumors, cysts, lesions, hemorrhages, or blood pools within any part of human anatomy. The anatomy may be a blood vessel, as an artery or a vein of a subject's vascular system, including cardiac vasculature, peripheral vasculature, neural vasculature, renal vasculature, and/or any other suitable lumen inside the body. In addition to natural structures, the present disclosure can be implemented in the context of man-made structures such as, but without limitation, heart valves, stents, shunts, filters, implants and other devices.

The beamformer 114 is coupled to the transducer array 112. The beamformer 114 controls the transducer array 112, for example, for transmission of the ultrasound signals and reception of the ultrasound echo signals. In some aspects, the beamformer 114 may apply a time-delay to signals sent to individual acoustic transducers within an array in the transducer 112 such that an acoustic signal is steered in any suitable direction propagating away from the probe 110. The beamformer 114 may further provide image signals to the processor circuit 116 based on the response of the received ultrasound echo signals. The beamformer 114 may include multiple stages of beamforming. The beamforming can reduce the number of signal lines for coupling to the processor circuit 116. In some aspects, the transducer array 112 in combination with the beamformer 114 may be referred to as an ultrasound imaging component.

The processor 116 is coupled to the beamformer 114. The processor 116 may also be described as a processor circuit, which can include other components in communication with the processor 116, such as a memory, beamformer 114, communication interface 118, and/or other suitable components. The processor 116 may include a central processing unit (CPU), a graphical processing unit (GPU), a digital signal processor (DSP), an application specific integrated circuit (ASIC), a controller, a field programmable gate array (FPGA) device, another hardware device, a firmware device, or any combination thereof configured to perform the operations described herein. The processor 116 may also be implemented as a combination of computing devices, e.g., a combination of a DSP and a microprocessor, a plurality of microprocessors, one or more microprocessors in conjunction with a DSP core, or any other such configuration. The processor 116 is configured to process the beamformed image signals. For example, the processor 116 may perform filtering and/or quadrature demodulation to condition the image signals. The processor 116 and/or 134 can be configured to control the array 112 to obtain ultrasound data associated with the object 105.

The communication interface 118 is coupled to the processor 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processor 134 is coupled to the communication interface 136. The processor 134 may also be described as a processor circuit, which can include other components in communication with the processor 134, such as the memory 138, the communication interface 136, and/or other suitable components. The processor 134 may be implemented as a combination of software components and hardware components. The processor 134 may include a central processing unit (CPU), a graphics processing unit (GPU), a digital signal processor (DSP), an application-specific integrated circuit (ASIC), a controller, an FPGA device, another hardware device, a firmware device, or any combination thereof configured to perform the operations described herein. The processor 134 may also be implemented as a combination of computing devices, e.g., a combination of a DSP and a microprocessor, a plurality of microprocessors, one or more microprocessors in conjunction with a DSP core, or any other such configuration. The processor 134 can be configured to generate image data from the image signals received from the probe 110. The processor 134 can apply advanced signal processing and/or image processing techniques to the image signals. In some aspects, the processor 134 can form a three-dimensional (3D) volume image from the image data. In some aspects, the processor 134 can perform real-time processing on the image data to provide a streaming video of ultrasound images of the object 105. In some aspects, the host 130 includes a beamformer. For example, the processor 134 can be part of and/or otherwise in communication with such a beamformer. The beamformer in the in the host 130 can be a system beamformer or a main beamformer (providing one or more subsequent stages of beamforming), while the beamformer 114 is a probe beamformer or micro-beamformer (providing one or more initial stages of beamforming).

The memory 138 is coupled to the processor 134. The memory 138 may be any suitable storage device, such as a cache memory (e.g., a cache memory of the processor 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory.

The memory 138 can be configured to store subject information, measurements, data, or files relating to a subject's medical history, history of procedures performed, anatomical or biological features, characteristics, or medical conditions associated with a subject, computer readable instructions, such as code, software, or other application, as well as any other suitable information or data. The memory 138 may be located within the host 130. Subject information may include measurements, data, files, other forms of medical history, such as but not limited to ultrasound images, ultrasound videos, and/or any imaging information relating to the subject's anatomy. The subject information may include parameters related to an imaging procedure such as an anatomical scan window, a probe orientation, and/or the subject position during an imaging procedure. The memory 138 can also be configured to store information related to the training and implementation of machine learning algorithms (e.g., neural networks) and/or information related to implementing image recognition algorithms for detecting/segmenting anatomy, image quantification algorithms, and/or image acquisition guidance algorithms, including those described herein.

The display 132 is coupled to the processor circuit 134. The display 132 may be a monitor or any suitable display. The display 132 is configured to display the ultrasound images, image videos, and/or any imaging information of the object 105.

The ultrasound imaging system 100 may be used to assist a sonographer in performing an ultrasound scan. The scan may be performed in a at a point-of-care setting. In some instances, the host 130 is a console or movable cart. In some instances, the host 130 may be a mobile device, such as a tablet, a mobile phone, or portable computer. During an imaging procedure, the ultrasound system can acquire an ultrasound image of a particular region of interest within a subject's anatomy. The ultrasound imaging system 100 may then analyze the ultrasound image to identify various parameters associated with the acquisition of the image such as the scan window, the probe orientation, the subject position, and/or other parameters. The ultrasound imaging system 100 may then store the image and these associated parameters in the memory 138. At a subsequent imaging procedure, the ultrasound imaging system 100 may retrieve the previously acquired ultrasound image and associated parameters for display to a user which may be used to guide the user of the ultrasound imaging system 100 to use the same or similar parameters in the subsequent imaging procedure, as will be described in more detail hereafter.

In some aspects, the processor 134 may utilize deep learning-based prediction networks to identify parameters of an ultrasound image, including an anatomical scan window, probe orientation, subject position, and/or other parameters. In some aspects, the processor 134 may receive metrics or perform various calculations relating to the region of interest imaged or the subject's physiological state during an imaging procedure. These metrics and/or calculations may also be displayed to the sonographer or other user via the display 132.

Before continuing, it should be noted that the examples described above are provided for purposes of illustration, and are not intended to be limiting. Other devices and/or device configurations may be utilized to carry out the operations described herein.

For example, the example above may be used to implement a method for free fluid estimation of claim 1, wherein the identifying the region of free fluid comprises identification of a first region and a second region different from the first region; and the data set comprises a first data set and a second data set different from the first. The method for free fluid estimation may include the first data set is organized through a first trained neural network based on annotation of previously captured images and free fluid regions corresponding to the first region and wherein the second data set is organized through a second trained neural network based on annotation of previously captured images and free fluid regions corresponding to the second region. In an example, a method for free fluid estimation may include a case where the image comprises a first section of data and a second section of data distinct from the first section and also the first section of data is pre-processed to be used as an input for a first trained model while the second section of data is pre-processed for use in a second trained model, wherein the pre-processing for use in the first trained model is distinct from the pre-processing for use in the second trained model.

Other examples include pre-processing variations that can vary in the way the data for at least one of the first section and the section are modified through at least one of resizing, normalization, data augmentation by applying transformations such as rotation, flipping, cropping, color shifting to the input images, feature extraction, and dimensionality reduction.

The above methods may be implemented on systems using processors as well as using memory and other non-transitory computer-readable mediums.

Figure 2:
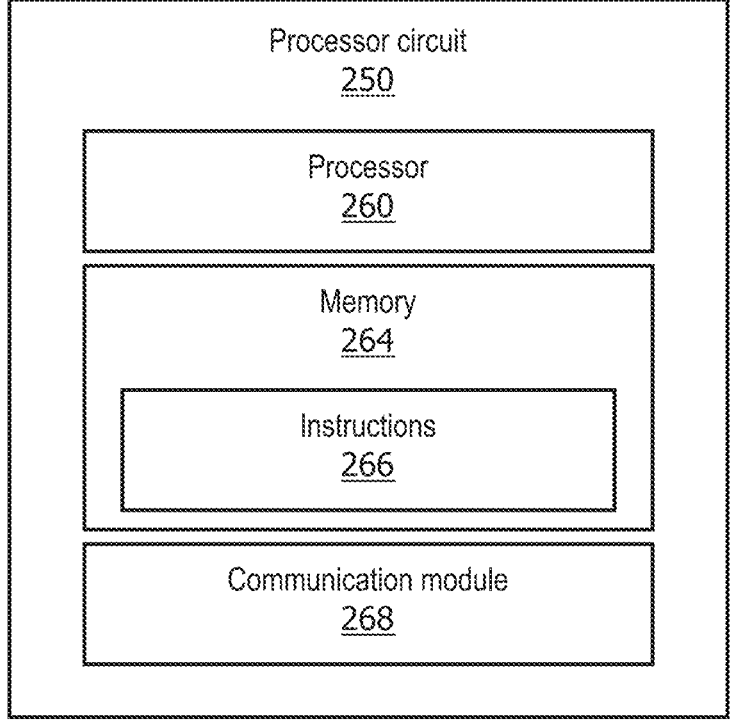
FIG. 2 is a schematic diagram of a processor circuit, according to aspects of the present disclosure.

FIG. 2 is a schematic diagram of a processor circuit 250, according to aspects of the present disclosure. The processor circuit 250 may be implemented in the ultrasound imaging system 100, or other devices or workstations (e.g., third-party workstations, network routers, etc.), or on a cloud processor or other remote processing unit, as necessary to implement the method. As shown, the processor circuit 250 may include a processor 260, a memory 264, and a communication module 268. These elements may be in direct or indirect communication with each other, for example via one or more buses.

The processor 260 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 260 may also comprise another hardware device, a firmware device, or any combination thereof configured to perform the operations described herein. The processor 260 may also be implemented as a combination of computing devices, e.g., a combination of a DSP and a microprocessor, a plurality of microprocessors, one or more microprocessors in conjunction with a DSP core, or any other such configuration.

The memory 264 may include a cache memory (e.g., a cache memory of the processor 260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an aspect, the memory 264 includes a non-transitory computer-readable medium. The memory 264 may store instructions 266. The instructions 266 may include instructions that, when executed by the processor 260, cause the processor 260 to perform the operations described herein. Instructions 266 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 268 can include any electronic circuitry and/or logic circuitry to facilitate direct or indirect communication of data between the processor circuit 250, and other processors or devices. In that regard, the communication module 268 can be an input/output (I/O) device. In some instances, the communication module 268 facilitates direct or indirect communication between various elements of the processor circuit 250 and/or the ultrasound imaging system 100. The communication module 268 may communicate within the processor circuit 250 through numerous methods or protocols. Serial communication protocols may include but are not limited to United States Serial Protocol Interface (US SPI), Inter-Integrated Circuit (I2C), Recommended Standard 232 (RS-232), RS-485, Controller Area Network (CAN), Ethernet, Aeronautical Radio, Incorporated 429 (ARINC 429), MODBUS, Military Standard 1553 (MIL-STD-1553), or any other suitable method or protocol. Parallel protocols include but are not limited to Industry Standard Architecture (ISA), Advanced Technology Attachment (ATA), Small Computer System Interface (SCSI), Peripheral Component Interconnect (PCI), Institute of Electrical and Electronics Engineers 488 (IEEE-488), IEEE-1284, and other suitable protocols. Where appropriate, serial and parallel communications may be bridged by a Universal Asynchronous Receiver Transmitter (UART), Universal Synchronous Receiver Transmitter (USART), or other appropriate subsystem.

External communication (including but not limited to software updates, firmware updates, model sharing between the processor and central server, or readings from the ultrasound imaging system 100) may be accomplished using any suitable wireless or wired communication technology, such as a cable interface such as a universal serial bus (USB), micro USB, Lightning, or FireWire interface, Bluetooth, Wi-Fi, ZigBee, Li-Fi, or cellular data connections such as 2G/GSM (global system for mobiles), 3G/UMTS (universal mobile telecommunications system), 4G, long term evolution (LTE), WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

Figure 3:
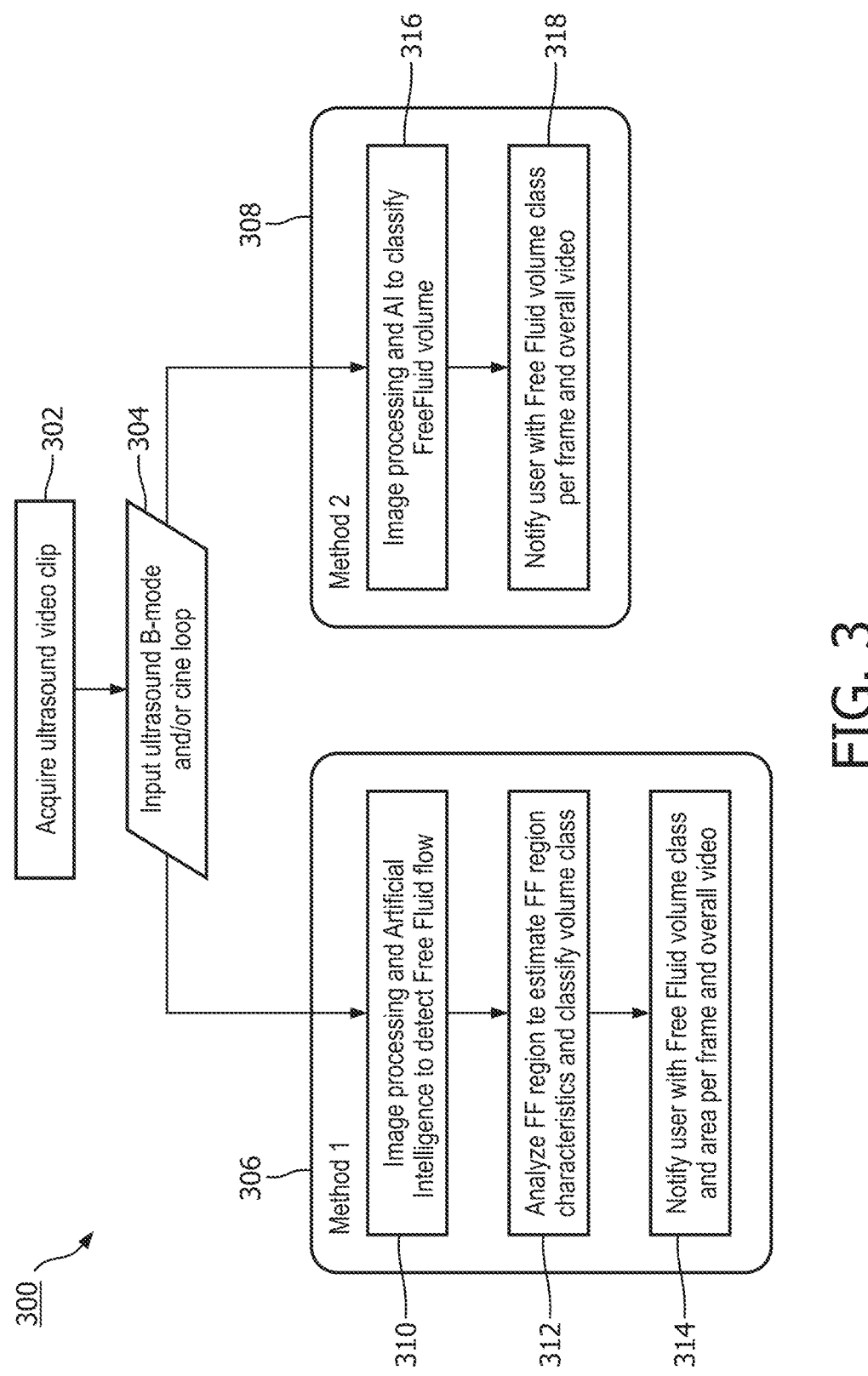
FIG. 3 shows an example of a method for detecting free fluid volume class by combining image processing and artificial intelligence in 2D imaging.

FIG. 3 shows an example of a method 300 for detecting free fluid volume class by combining image processing and artificial intelligence in 2D ultrasound imaging. While the present discussion focuses on 2D ultrasound imaging some of the techniques may also be used in other ultrasound formats.

At block 302, the method 300 begins with the acquisition of an ultrasound video clip. The clip may include a number of image frames generated from received ultrasound signals. The ultrasound video clip may be provided by a local device such as an attached ultrasound transducer and probe, or may be provided by a remote device or other device not physically connected to a device receiving and processing the ultrasound video clip.

At block 304, an ultrasound video clip taken in B-mode may be provided as part of one or both sub-methods, seen in block 306 and 308. As used herein, B-mode may refer to a brightness mode of an ultrasound system where a linear array of transducers scans a plane through a subject that can be viewed as a two-dimensional image on screen. B-mode may also refer to or include a 2D imaging mode. In an example for block 304, the imaging mode provided may also or alternatively include cine loop, or a sequence of images from an ultrasound examination.

In method 1 shown in block 306, the provided ultrasound input is processed to output a free fluid volume class and an area. In method 2 shown in block 308, the provided ultrasound input is processed to output a free fluid volume class. The variance in outputs can be used to provide different levels of information based on at least one of (i) the skill level of the user, (ii) an ultrasound setting, (iii) a severity level, and (iv) a desired output function, for example for medical records, billing, printing, or display.

At block 310, each ultrasound input may have image processing applied where individual frame and/or groups of frames may be processed to identify anatomical features and the presence or absence of free fluid in a particular frame or group of frames. In an example, the processing may include artificial intelligence approaches including the processing of images through a neural network or other trained model. A trained model for identifying free fluid may have been trained using annotated images where free fluid is identified by clinicians. In an example, a trained model may include or use at least one of convolutional neural network, support vector machine, random forest, k-nearest neighbors, logistic regression, decision tree, naive bayes, gradient boosting. In an example, At block 312, an image that has been processed for detection of free fluid may have the area of the free fluid estimate and quantified. The quantification of the free fluid may make use of not only image analysis of an area identified as free fluid, but also surrounding identified anatomical structures. For example, an identified anatomical feature may provide context for the location of the free fluid within the body and provide context for the calculated area of identified free fluid in the particular frame. If a calculation of identified free fluid in an ultrasound is identified, this value can be compared to other measurements of free fluid in that particular region of the body that may be stored as part of a database, a set of ranges, a set of images used to train a machine learning model or neural network. This anatomical feature recognition may also be used in the comparison of the quantified free fluid area by further filtering of comparable ranges based on patient data and demographics that may be accessed or provided by the system. The volume class determination process is highly dependent on the organ or anatomical feature being scanned. For example, organs such as the heart and liver have different volume classes than organs such as the kidneys and spleen. Additionally, the volume class determination process is also responsive to anatomical feature detection. By comparing the volume classes of the organ or anatomical feature over time, the technician can determine if the treatment is having the desired effect.

Further, the type of data preprocessing for a particular model being applied to data may vary largely based on the particular organ. For example, if a model detects a first organ that has relatively simple features, minimal data preprocessing in the form of feature extraction may need to be performed prior to generating an output of a neural network used to output free fluid estimation. By contrast, if a model detects a second organ which suggests the local area around the second organ may have more complex features in the context of free-fluid detection, then different data preprocessing may need to occur prior to proving the acquired image data to a neural network in order to generate a volume class for that particular region.

For example, if a FAST exam were being performed and during the exam, the left upper quadrant (LUQ) of a patient used a first trained model to estimate free fluid in that region while a right upper quadrant of a patient used a second trained model to estimate free fluid in that region, the system would be able to use organ or anatomical feature detection to change which trained model was applied to which incoming data. Indeed, as the data was being acquired using for example an ultrasound probe, the model being applied could switch from one model to the next in response to a detection of an organ or an anatomical feature. Further, not only could the model being used to estimate free fluid, but the pre-processing of the data being acquired, e.g. by an ultrasound transducer could change to correspond to the particular model being used. For example, data in differing regions may need to be pre-processed through resizing, normalization, data augmentation by applying transformations such as rotation, flipping, cropping, and color shifting to the input images, feature extraction, or dimensionality reduction. If a first organ is detected, a first associated pre-processing step may be applied and if a second organ is detected, a second associated pre-processing step may be applied. These various pre-processing steps may occur at a time overlapping with the time during which data is being acquired. Further, the various pre-processing steps may switch from a first pre-processing to a second pre-processing as the data is being acquired and the physical location of the data acquirer, such as a transducer, is moved relative to a subject of the ultrasound examination.

At block 314, the method 300 may include notification of a user. The user may refer to a patient, provider, or may also include storage of the information in a system in a format for printing, billing, displaying, or charting in medical records in a connected system. The notification may include the quantification of the free fluid area using numerical values describing the area or estimate volume of the free fluid identified. The notification may also include a free fluid volume class estimation whereby the quantified free fluid is categorized into various levels of severity or placed on a scale showing how the level of identified free fluid compares to the expected range, previously measured range, clinically significant range or other contextual information. As indicated above, this volume class information may be obtained based on a detection of anatomical features identified in the same ultrasound image as the free fluid. Using this anatomical identification, free fluid ranges for that particular region of the body may be retrieved or used to place the presently measured free fluid quantification values in context.

In block 314, both a quantification of free fluid and a free fluid volume class may be identified and calculated on a per frame basis and provided to a user. Providing both a quantification and a contextual and relative volume class identification allows a trained professional, billing department, or medical record system to have specific measured values to make determinations from, for example, relating to a billing code where different amounts of free fluid measured could relate to different billing codes. In an example, an output volume class and free fluid quantified values could be generated for a number of different anatomical regions seen over the course of an image scan. For example, if the ultrasound images include scans from a right upper quadrant of a patient and the left upper quadrant of the patient, the output notification could include notifications demarcated by each of these regions of the body.

In the method 2 in block 308, a second sub-method may be pursued in parallel, in sequence, or in the alternative to method 1 showing in block 306. Method 2 in block 308 relates to providing a volume class identification without a quantification. In an example, this may be useful in faster-paced settings and/or for non-expert users where the exact quantification and measure of the free fluid is less important than a contextual provision of the severity of the free fluid amount. In order to provide this contextual information, detection, quantification, and identification of anatomical regions can be utilized.

In block 316, the ultrasound image input, such as B-mode images and/or cine loop input can be processed using AI technique such as image recognition, computer vision techniques, deep learning techniques, neural networks, or other image processing approaches that can identify from ultrasound images regions as free fluid regions and any anatomical features as anatomical features. Both of these identifications though are used to identify not only a free fluid area, but also an anatomical region based on identified anatomical structures or landmarks in the body. Based on an identified anatomical region or landmark, the method 2 308 may retrieve and/or provide information about free fluid readings in that particular anatomical region or related to the anatomical structure identified to include and/or be adjacent to a region of free fluid. Based on this information and on the identified and quantified area of free fluid, the measure of the free fluid identified in an ultrasound image may be placed into a volume class.

In an example, a volume class may be binary such as high or low, referring to a high or low volume of free fluid detected in the ultrasound input or ultrasound image frame. In an example, a volume class may be binary such as severe or non-severe or other related language associated with a clinical setting such as urgent or non-urgent. In an example the volume class may refer to placement of a measured free fluid region along a continuous scale ranging from high to low at each end referring to a relatively high amount of free fluid or a relatively low amount of free fluid. The ranges of free fluid severity for a particular region can vary from anatomical region to region. Accordingly, and for example, if an ultrasound image moves from one anatomical region to another, the scale and volume class determination could change based on what is considered high or low amounts of free fluid for that particular region of the body.

In an example, an ultrasound cine loop could move where a portion of the lungs are visible to a portion of the body where the liver is visible in the ultrasound image frame. If there is free fluid in both regions, the free fluid could be quantified in the image, but also placed on a scale or into a volume class where that measure of free fluid is contextually compared to other free fluid values for that particular anatomical region. In an example, the scale ranging from high to low for free fluid comparisons may be linear, nonlinear, logarithmic, non-continuous, bucketized, or any other representation of a detected free fluid compared to ranges obtained from a larger data set. The larger data set may be pulled from, for example, a hospital system, a patient history for a particular patient being examined, a trained neural network model based on annotated images of ultrasounds, or any other data set useful to develop a range or ranges for comparison to identified free fluid regions.

At block 318, of the method 300, a user can be notified of the free fluid volume class. This notification can be on a per frame basis or for an entire cine loop based on averaging or aggregation of readings and volume class classifications. In an example, an output volume class could be generated for a number of different anatomical regions seen over the course of an image scan. For example, if the ultrasound images include scans from a right upper quadrant of a patient and the left upper quadrant of the patient, the output notification could include notifications demarcated by each of these various regions of the body and provide a subset list of regions based on the areas identified in the scan.

The method 300 may assist with interpretation support with respect to the absolute and relative size of the free fluid visualized during the exam. The present disclosure further provides techniques that enable quantification and relative assessment of free fluid size that can be used in clinical scenarios for users who may not perform FAST exams often.

The free fluid volume class can be estimated using the algorithm ultrasound imaging. In Method 1 306, the free fluid regions can be initially detected using a combination of image processing and AI algorithms. The detected free fluid region can then be further analyzed to estimate the area of the region and the results can be displayed to the user in various formats such as:

(a) The size of the exam (area or some other metric) relative to a what is known to be a large free fluid size based on a data set representative of the distribution of fluid sizes that are observed with the FAST exam.

(b) Largest area of free fluid in the entire video/clip (c) Area of free fluid as an absolute value or percentage of the image in each frame (d) Overall volume class of the free fluid in the entire video/clip In method 2 308, a combination of image processing and AI algorithms can be used to classify the ultrasound image for different volume class such as small and large. The AI algorithm may be trained using the ground truth annotation of images with different volume class. The AI algorithm then can learn from the different features and predict the volume class of the free fluid. The ground truth could be derived from CT imagery and/or expert opinion.

Figure 4:
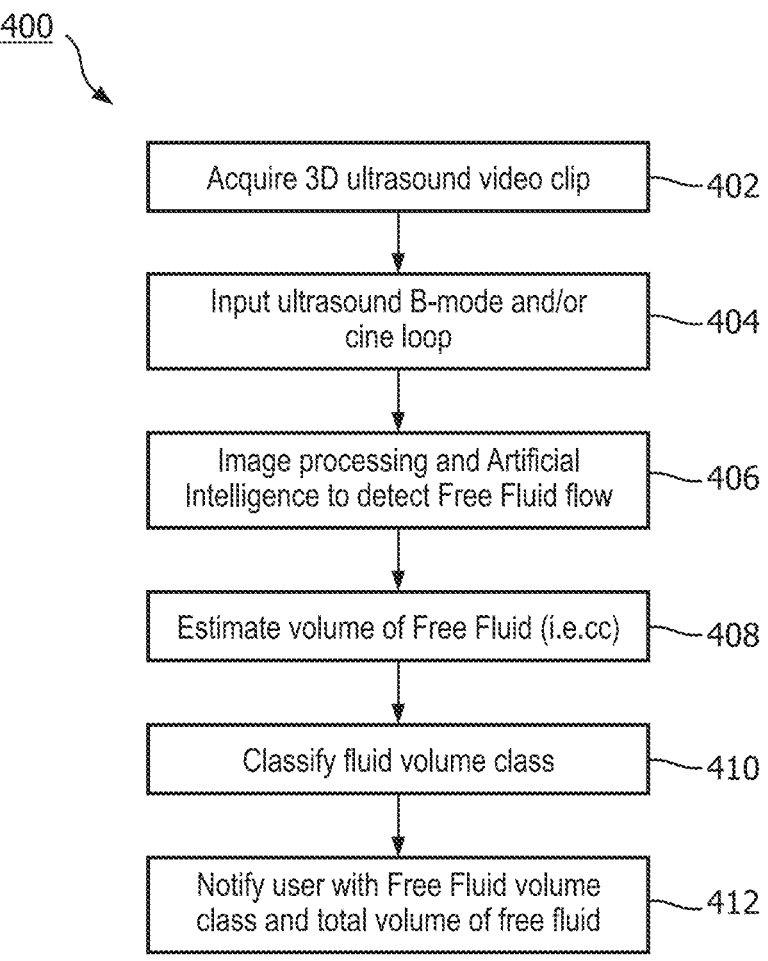
FIG. 4 illustrates an example of a method for detecting free fluid volume class by combining image processing and artificial intelligence in 3D imaging.

FIG. 4 illustrates an example of a 3D method 200 for detecting free fluid volume class by combining image processing and artificial intelligence in 3D ultrasound imaging. Some of the ideas disclosed with regards to FIG. 3 may be included and incorporated here.

At block 402, a 3D ultrasound video clip can be acquired. In an example the video clip may be acquired by a transducer physically connected to the device processing the video clip, and may alternatively acquired by a transducer remote from the device processing the video clip.

At block 404, the 3D ultrasound information may be provided in a B-mode and/or cine loop format as input for further image processing and free fluid detection. In an example, the input may be gained through 3D ultrasound image generation such as through a composition of images gathered through probe movement or through beam steering to obtain a number of images at a particular location on the patient.

At block 406, the ultrasound input images of block 404 may be used in image processing and comparison using artificial intelligence algorithms. In an example, each ultrasound input may have image processing applied for 3D ultrasound where individual frame and/or groups of frames composed as 3D ultrasound images may be processed to identify anatomical features and the presence or absence of free fluid in a particular frame or group of frames. In an example, the processing may include artificial intelligence approaches including the processing of 3D images through a neural network or other trained model. A trained model for identifying free fluid may have been trained using annotated images where free fluid is identified by clinicians.

At block 408, an estimate of free fluid volume may be made based on the image processing that occurred in block 406. In an example, the estimation of free fluid may be measured in quantified terms such as cubic centimeters (ccs).

At block 410, the 3D method 400 may use outside data sets to identify a range of values considered to be clinically relevant for a particular free fluid reading and may classify the free fluid volume identified in block 408 relative to that particular data set in order to determine a free fluid volume class. In an example, the free fluid class may be one of a binary representing a high or low amount of free fluid represented as a volume class. In an example, the free fluid volume class may be represented as a position along a scale that may be at least one of continuous, linear, non-linear, logarithmic, or bucketized.

At block 412, the 3D method 400 may use the classification of the free fluid measurement into the volume class in order to provide a representation of the volume class. In an example, the provision of the volume class to a user can take the form of a notification, a display of the volume class within a scale on same screen as the ultrasound image, a notation in a medical record, a notation or file in a medical billing file, a transmitted image to a remote device, or any other method for notifying the user of the free fluid volume class. In an example, the notification of the user of the free fluid volume class may include a quantified representation of the free fluid volume identified. In an example, the notification to the user of the free fluid volume class may not include a quantified and numerical representation of the free fluid volume identified and instead provide the volume class represented as a representation of the free fluid along a graphically depicted scale. In an example, the free fluid may be represented through binary categories of free fluid based on the volume class determined for that particular measurement of free fluid compared to a data set of past free fluid measurements.

This algorithm can also be used for 3D ultrasound imaging as shown in FIG. 4. In an 3D ultrasound scan each imaging plane is registered to a reference frame and hence all the frames can be used to create a volumetric space. Free fluid regions in each frame can be detected using a combination of image processing and AI algorithms similar to 2D case. These detected regions in each frame can be stacked to form a 3D volume with registration of each image to the scanned volumetric space. Therefore, the total volume of free fluid (i.e. in cc) can be estimated based on area of the free fluid in each frame and the distance between each consecutive frame. Similarly, various formats similar to discussed above can be used to display it to the user such as the overall free fluid volume class, the total volume of fluid in the scanned region, and the slice with the highest free fluid area in the 3D volume scan.

Figure 5:
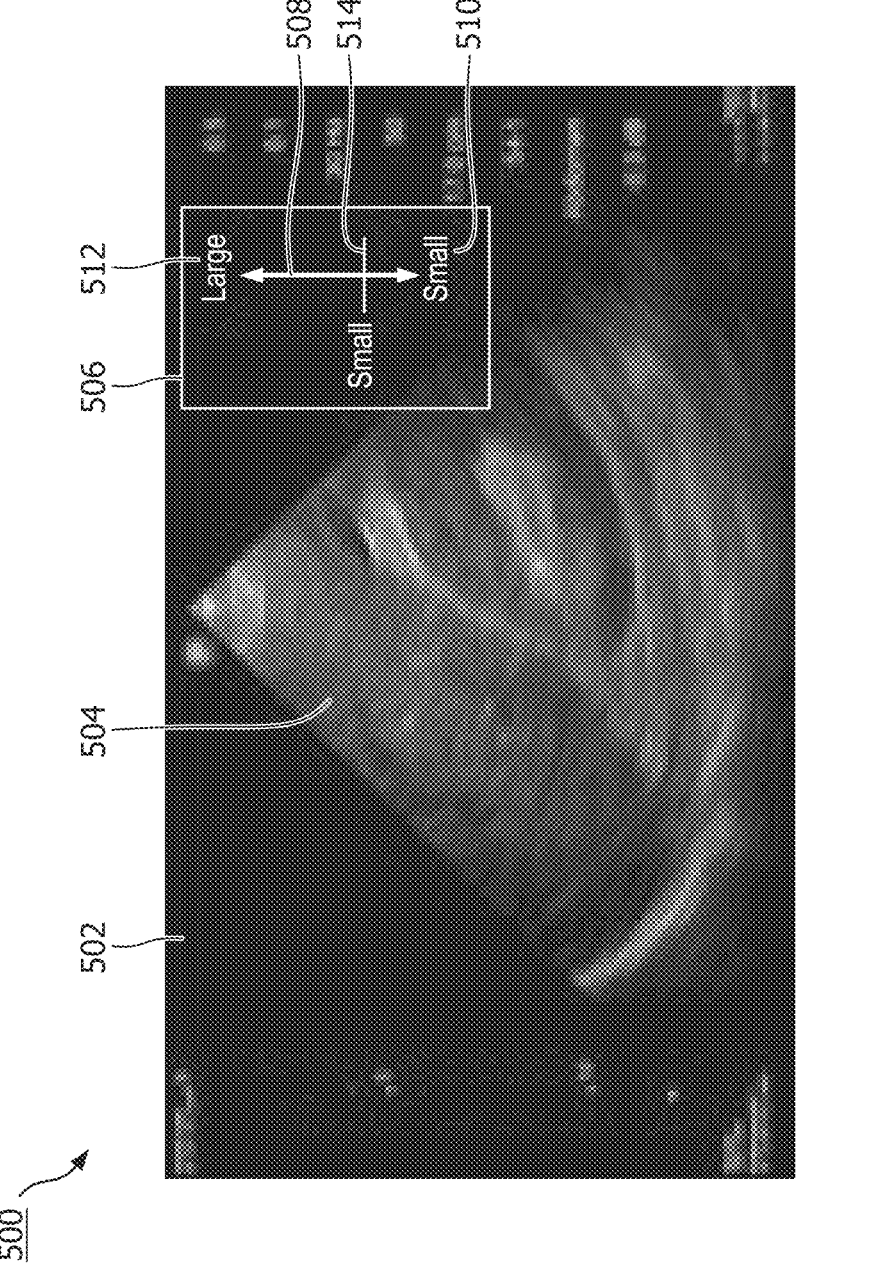
FIG. 5 illustrates an example of a user interface displaying the free fluid detected is reported on a relative scale.

FIG. 5 illustrates an example of a user interface 500 displaying the free fluid detected is reported on a relative scale. The user interface 500 may include a display 502 of an ultrasound image 504 and a representation graphic 506 of the free fluid identified in the ultrasound image. In an example, the representation graphic 506 of the free fluid identified in the image may include a scale 508 where there is a first value 510 and a second value 512 representing opposing ends of the scale 508. In an example the first value 510 and the second value 512 may represent two various categories of free fluid levels identified compared to a data set or range of value for free fluid obtained from previous medical imaging. In an example, the representation graphic 506 may include a free fluid estimation indicator 514 where the measured value for free fluid in a particular image frame may be shown relative to the context provided by the scale 508. In an example, the scale 508 may be continuous, discontinuous, linear, or non-linear. In an example the scale can be reflected by a binary of categories such as low and high levels of free fluid. In an example the scale can be reflected by multiple categories of free fluid levels with the free fluid estimation indicator 514 graphically located among the multiple categories to reflect the estimated level of free fluid detected.

Additionally, the present disclosure provides a system that classify/score free fluid volume class in an ultrasound scan based on image processing and AI based image interpretation. The present system relates to the following elements, a method for presenting free fluid size on a relative scale, a method for presenting free fluid size on an absolute scale, an algorithm to estimate area of free fluid in a frame, an algorithm to display percentage coverage of free fluid in a frame, an algorithm to display the frame to user that contain the largest amount of free fluid area in a video clip, an algorithm to identify frames with free fluid area above a defined threshold, and algorithm to classify free fluid volume class, and algorithm to estimate fluid volume from a 3D ultrasound scan.

In another example, a 3D volume could be estimated from a 2D array transducer using two orthogonal 2D image planes or many planes at various orientations. This disclosed method may allow for faster volume estimation by acquiring fewer frames to estimate a volume.

The device could also display the free fluid size on a relative scale. The relative scale is established based on datasets that capture the range of free fluid sizes that are representative of the free fluid size ranges that users may encounter in practice. The scale could be linear, non-linear, peace-wise linear, continuous or discrete. The maximum and minimum size may be based on pre-determined thresholds or the smallest and largest fluid volumes in the database. The scale could be adjusted based on the transducer type, transducer sector width, depth, and gain settings.

In another approach a 3D volume could be estimated from imagery acquired with a 2D imaging probe by stitching together multiple 2D images from a dynamic (user/human motion or machine motion) sweep into a volume.

The invention claimed is:

1. A method for free fluid estimation, comprising:
   identifying a region of free fluid in an image;
   calculating a free fluid measure based on the region of free fluid identified in the image;
   generating a volume class for the region of free fluid in the image, wherein the volume class is generated by comparison of the free fluid measure to a data set of previously stored free fluid measures; and
   outputting a representation of the volume class to a graphical representation for display,
   wherein the graphical representation includes the volume class displayed in the context of at least one of:
       a binary classification;
       a linear scale;
       a plurality of severity levels;
       a non-linear scale;
       a numerical value; and
       a numerical range.

2. The method for free fluid estimation of claim 1, comprising:
   identifying an anatomical structure in the image;

selecting a subset of the data set of previously stored free fluid measures in response to
   the anatomical structure identified in the image.

3. The method for free fluid estimation of claim 1, comprising outputting a representation of the volume class to at least one of:
   a graphical representation for display;
   a format for billing documentation;
   a format for medical record documentation; and
   a format for digital storage.

4. The method for free fluid estimation of claim 1, wherein the data set is organized through a trained neural network based on annotation of previously captured images and free fluid regions.

5. The method for free fluid estimation of claim 1, wherein the identifying the region of free fluid comprises identification of a first region and a second region different from the first region; and the data set comprises a first data set and a second data set different from the first.

6. The method for free fluid estimation of claim 5, wherein:
   the first data set is organized through a first trained neural network based on annotation of previously captured images and free fluid regions corresponding to the first region; and
   the second data set is organized through a second trained neural network based on annotation of previously captured images and free fluid regions corresponding to the second region.

7. The method for free fluid estimation of claim 5, wherein:
   the image comprises a first section of data and a second section of data distinct from the first section;
   the first section of data is pre-processed to be used as an input for a first trained model; and
   the second section of data is pre-processed for use in a second trained model, wherein the pre-processing for use in the first trained model is distinct from the pre-processing for use in the second trained model.

8. The method of claim 7, wherein the pre-processing variations can include variations in the way the data for at least one of the first section and the section are modified through at least one of resizing, normalization, data augmentation by applying transformations such as rotation, flipping, cropping, color shifting to the input images, feature extraction, and dimensionality reduction.

9. The method for free fluid estimation of claim 1, wherein the diagnostic images are obtained by at least one:
   ultrasound imaging;
   computerized tomography imaging; and
   magnetic resonance imaging.

10. A system for free fluid estimation, comprising:
   a processor; and
   a memory comprising instructions that when executed on the processor, cause the processor to:
       identify a region of free fluid in an diagnostic image;
       calculate a free fluid measure based on the region of free fluid identified in the diagnostic image; and
       generate a volume class for the region of free fluid in the diagnostic image, wherein the volume class is generated by comparison of the free fluid measure to a data set of previously stored free fluid measures; and
       output a representation of the volume class to a graphical representation for display,
           wherein the graphical representation includes the volume class displayed in the context of at least one of:
               a binary classification;

a linear scale;

a plurality of severity levels;

a non-linear scale;

a numerical value; and a numerical range.

11. The system for free fluid estimation of claim 10, wherein the memory further comprises instructions that when executed on the processor cause the processor to:

identify an anatomical structure in the image; and select a subset of the data set of previously stored free fluid measures in response to the anatomical structure identified in the image.

12. The system for free fluid estimation of claim 10, wherein the memory further comprises instructions that when executed on the processor cause the processor to output a representation of the volume class to at least one of:

a graphical representation for display;

a format for billing documentation;

a format for medical record documentation; and a format for digital storage.

13. The system for free fluid estimation of claim 10, wherein the data set is organized through a trained neural network based on annotation of previously captured images and free fluid regions.

14. A non-transitory computer-readable medium comprising instructions that when executed on a processor cause the processor to:

identify a region of free fluid in an diagnostic image;

calculate a free fluid measure based on the region of free fluid identified in the diagnostic image; and generate a volume class for the region of free fluid in the diagnostic image, wherein the volume class is generated by comparison of the free fluid measure to a data set of previously stored free fluid measures; and output a representation of the volume class to a graphical representation for display, wherein the graphical representation includes the volume class displayed in the context of at least one of:

a binary classification;

a linear scale;

a plurality of severity levels;

a non-linear scale;

a numerical value; and a numerical range.

15. The non-transitory computer-readable medium of claim 14, further comprising instructions that when executed on a processor cause the processor to:

identify an anatomical structure in the image; and select a subset of the data set of previously stored free fluid measures in response to the anatomical structure identified in the image.

16. The non-transitory computer-readable medium of claim 14, further comprising instructions that when executed on a processor cause the processor to output a representation of the volume class to at least one of:

a graphical representation for display;

a format for billing documentation;

a format for medical record documentation; and a format for digital storage.

17. The non-transitory computer-readable medium of claim 14, wherein the data set is organized through a trained neural network based on annotation of previously captured images and free fluid regions.

* * * * *